United States Patent
Müller et al.

(10) Patent No.: US 6,409,921 B1
(45) Date of Patent: Jun. 25, 2002

(54) INTEGRALLY ASYMMETRICAL POLYOLEFIN MEMBRANE FOR GAS EXCHANGE

(75) Inventors: Marcus O. Müller, Arnhem (NL); Erich Kessler, Hoschst im Odenw (DE); Ralf R. Hornscheidt, Heiligenhaus (DE); Frank Wiese, Wuppertal (DE); Armin J. Lang, Miltenberg (DE)

(73) Assignee: Membrana GmbH, Wuppertal (DE)

( * ) Notice: Subject to any disclaimer, the term of this patent is extended or adjusted under 35 U.S.C. 154(b) by 0 days.

(21) Appl. No.: 09/463,316

(22) PCT Filed: Jul. 16, 1998

(86) PCT No.: PCT/EP98/04451

§ 371 (c)(1),
(2), (4) Date: Feb. 28, 2000

(87) PCT Pub. No.: WO99/04891

PCT Pub. Date: Feb. 4, 1999

(30) Foreign Application Priority Data

Jul. 23, 1997 (DE) .......................... 197 31 677

(51) Int. Cl.[7] .......................... A61M 1/18; B01D 63/02; B01D 61/00
(52) U.S. Cl. ....................... 210/644; 210/483; 210/488; 210/489; 210/490; 210/500.21; 210/500.23; 210/500.36; 210/645; 264/41; 422/42; 422/45; 422/48
(58) Field of Search ................. 210/500.21, 500.23, 210/500.36, 644, 645, 483, 488, 489, 490; 264/41; 422/42, 45, 48

(56) References Cited

U.S. PATENT DOCUMENTS 4,594,207 A 6/1986 Josefiak et al. ............... 264/41
5,192,320 A 3/1993 Anazawa et al. ............. 623/12

FOREIGN PATENT DOCUMENTS

| DE | 27 37 745 A | 3/1978 |
|---|---|---|
| DE | 28 33 493 A | 2/1980 |
| DE | 32 05 289 A | 8/1983 |
| DE | 42 26 205 A | 2/1993 |
| EP | 133882 A | 6/1984 |
| EP | 285 812 A | 10/1988 |
| EP | 299381 A | 1/1989 |
| JP | 58 029839 A | 2/1983 |

OTHER PUBLICATIONS

Derwent Abstract AN 83–31173k (Undated).

Primary Examiner—John Kim
(74) Attorney, Agent, or Firm—Oliff & Berridge, PLC (57) ABSTRACT

Process for producing hydrophobic polyolefinic membranes for gas exchange via thermally induced liquid-liquid phase separation is disclosed. A solution of at least one polyolefin in a solvent system, of a compound A and a compound B having a viscosity less than 60 mPa s, is extruded to form a shaped object. The compound A is a solvent and compound B preferably a non-solvent of the polymer, and the boiling point of compound A is at least 50° C. higher than that of compound B. After the shaped object leaves the die, at least one surface thereof is subjected to an atmosphere promoting evaporation of compound B, and the shaped object is subsequently cooled until the phase separation and solidification of the high-polymer-content phase take place. The integrally asymmetrical membrane producible in this manner has a porosity of greater than 50% to 75% by volume, a sponge-like, open-pored, microporous support layer without macrovoids and on average isotropic pores, and at least one separation layer with pores <100 nm, if any. The membrane is preferably used for blood oxygenation.

31 Claims, 5 Drawing Sheets

INTEGRALLY ASYMMETRICAL POLYOLEFIN MEMBRANE FOR GAS EXCHANGE

BACKGROUND OF THE INVENTION

1. Field of the Invention

The invention relates to a process for producing a hydrophobic membrane using a thermally induced phase separation process, the membrane having a sponge-like, open-pored, microporous structure. The invention relates further to an integrally asymmetrical, hydrophobic membrane for gas exchange that is composed primarily of at least one polymer selected from the group of polyolefins and has a first and a second surface, the membrane having a support layer with an open-pored, microporous structure and adjacent to this support layer at least at one of the surfaces a separation layer with denser structure, and to the use of such membrane for blood oxygenation.

2. Description of Related Art

In a multitude of applications in the fields of chemistry, biochemistry, or medicine, the problem arises of separating gaseous components from liquids or adding such components to the liquids. For such gas exchange processes, there is increasing use of membranes that serve as a separation membrane between the respective liquid, from which a gaseous component is to be separated or to which a gaseous component is to be added, and a fluid that absorbs or releases this gaseous component. The fluid in this case can be either a gas or a liquid containing the gas component to be exchanged or capable of absorbing it. Using such membranes, an exchange surface can be provided for gas exchange and, if required, direct contact between the liquid and fluid can be avoided.

An important application of membrane-based gas exchange processes in the medical field is for oxygenators, also called artificial lungs. In these oxygenators, which are used in open-heart operations, for example, oxygenation of blood and removal of carbon dioxide from the blood take place. Generally, bundles of hollow-fiber membranes are used for such oxygenators. Venous blood flows in the exterior space around the hollow-fiber membranes, while air, oxygen-enriched air, or even pure oxygen is passed through the lumen of the hollow-fiber membranes. Via the membranes, there is contact between the blood and the gas, enabling transport of oxygen into the blood and simultaneously transport of carbon dioxide from the blood into the gas.

In order to provide the blood with sufficient oxygen and at the same time to remove carbon dioxide from the blood to a sufficient extent, the membranes must ensure a high degree of gas transport: a sufficient amount of oxygen must be transferred from the gas side of the membrane to the blood side and, conversely, a sufficient amount of carbon dioxide from the blood side of the membrane to the gas side, i.e., the transfer rates, expressed as the gas volume transported per unit of time and membrane surface area from one membrane side to the other, must be high. A decisive influence on the transfer rates is exerted by the porosity of the membrane, since only in the case of sufficiently high porosity can adequate transfer rates be attained.

A number of oxygenators are in use that contain hollow-fiber membranes with open-pored, microporous structure. One way to produce this type of membrane for gas exchange, such as for oxygenation, is described in DE-A-28 33 493. Using the process in accordance with this specification, membranes can be produced from meltable thermoplastic polymers with up to 90% by volume of interconnected pores. The process is based on a thermally induced phase separation process with liquid-liquid phase separation. In this process, a homogeneous single-phase melt mixture is first formed from the thermoplastic polymer and a compatible component that forms a binary system with the polymer, the system in the liquid state of aggregation having a range of full miscibility and a range with a miscibility gap, and this melt mixture is then extruded into a bath that is essentially inert with respect to the polymer and has a temperature lower than the demixing temperature. In this way, a liquid-liquid phase separation is initiated and the thermoplastic polymer solidified to form the membrane structure.

An improved process for producing such membranes, which permits specific adjustment of the pore volume, size, and wall, is disclosed in DE-A-32 05 289. In this process, 5–90% by weight of a polymer is dissolved, by heating to above the critical demixing temperature $T_c$, in 10–95% by weight of a mixture of two compounds that are liquid and miscible at the solution temperature, whereby the employed mixture of polymer and compounds A and B has a miscibility gap in the liquid state of aggregation, compound A is a solvent for the polymer, and compound B increases the phase separation temperature of a solution consisting of the polymer and compound A. The solution is then given shape and by cooling brought to demixing and solidifying, and the compounds A and B are subsequently extracted.

The membranes disclosed in accordance with DE-A-28 33 493 or DE-A-32 05 289 have an open-pored, microporous structure and also open-pored, microporous surfaces. On the one hand, this has the result that gaseous substances, such as oxygen or carbon dioxide, can pass through the membrane relatively unrestricted and the transport of a gas then takes place as a Knudsen flow or Knudsen diffusion, combined with relatively high transfer rates for gases. On the other hand, however, in extended use of these membranes in blood oxygenation or generally in gas exchange processes with aqueous liquids, blood plasma or a portion of the liquid can penetrate into the membrane and, in the extreme case, exit on the gas side of the membrane, even if in these cases the membranes are produced from hydrophobic polymers, in particular polyolefins. This results in a drastic decrease in gas transfer rates. For medical applications for blood oxygenation, this is termed plasma breakthrough.

The plasma breakthrough time of such membranes, as producible in accordance with DE-A-28 33 493 or DE-A-32 05 289, is sufficient in most cases of conventional blood oxygenation to oxygenate a patient in a normal open-heart operation. However, the desire exists for membranes with higher plasma breakthrough times in order to attain higher levels of safety in extended heart operations and to rule out the possibility of a plasma breakthrough that would require immediate replacement of the oxygenator. A frequently demanded minimum value in this connection for the plasma breakthrough time is 20 hours. The aim, however, is also to be able to oxygenate premature infants or in general patients with temporarily restricted lung function long enough until the lung function is restored, i.e., to be able to conduct long-term oxygenation. Prerequisites for this are appropriately long plasma breakthrough times.

From EP-A-299 381, hollow-fiber membranes for oxygenation are known that have plasma breakthrough times of more than 20 hours, i.e., there is no plasma breakthrough even under extended use. With the otherwise porous membrane with cellular structure, this is attained by a barrier layer that has an average thickness, calculated from the oxygen and nitrogen flow, not exceeding 2 μm and is substantially impervious to ethanol. The membrane is essentially free of open pores, i.e., pores that are open both to the outside and to the inside of the hollow-fiber membrane. The membranes in accordance with EP-A-299 381 have a porosity of at most 50% by volume, since at higher porosity values the pores are interconnected and communication occurs between the sides of the hollow-fiber membranes, resulting in plasma breakthrough. In the barrier layer, the transport of gases to be exchanged is effected by solution diffusion.

The production of these membranes is conducted via a melt-drawing process, i.e., the polymer is first melt-extruded to a form a hollow fiber and then hot- and cold-drawn. In this case, only relatively low porosity values are obtained, which means that, in conjunction with the transport occurring in the barrier layer via solution diffusion, the attainable transfer rates for oxygen and carbon dioxide remain relatively low. Moreover, while the hollow-fiber membranes in accordance with EP-A-299 381 exhibit sufficient tensile strength as a result of the pronounced drawing in conjunction with manufacture, they have only a small elongation at break. In subsequent textile processing steps, such as to produce bundles of hollow-fiber mats, which have proven excellent in the production of oxygenators with good exchange performance and as are described in EP-A-285 812, for example, these hollow-fiber membranes are therefore not conducive to processing.

Typically, in melt-drawing processes, membranes are formed with slit-shaped pores with pronounced anisotropy, the first main extension of which is perpendicular to the drawing direction and the second main extension perpendicular to the membrane surface, i.e., in the case of hollow-fiber membranes runs between the exterior and interior surfaces of the membrane, whereby the channels formed by the pores run in a relatively straight line between the surfaces. In the case in which, for example, mechanical damage in the spinning process causes leaks in the barrier layer, a preferred direction then exists for the flow of a liquid between the interior and exterior surfaces or vice-versa, thereby promoting plasma breakthrough.

SUMMARY OF THE INVENTION

It is therefore an object of the invention to provide a process with a wide variety of applications and with which membranes can be produced for gas exchange that exhibit only to a reduced extent, if at all, the disadvantages of the prior art membranes, permit high gas exchange performance, are impervious at least over extended periods of time to the breakthrough of hydrophilic liquids, in particular blood plasma, and have good qualities for further processing.

It is a further object of the invention to provide membranes for gas exchange in which the disadvantages of the prior art membranes are at least reduced, that have a high capacity for gas exchange, are resistant at least over extended periods of time to the breakthrough of hydrophilic liquids, in particular blood plasma, and exhibit good qualities for further processing.

DETAILED DESCRIPTION OF PREFERRED EMBODIMENTS.

The object is met by a process for producing a hydrophobic membrane having a sponge-like, like, open-pored, microporous structure, the process comprising at least the steps of:

a) dissolving of 20–90% by weight of at least one polymer, selected from the group of polyolefins, by heating to above the critical demixing temperature in 80–10% by weight of a mixture of two compounds A and B that form the solvent system and are liquid and miscible at the dissolving temperature, whereby the employed mixture of polymer and compounds A and B has a miscibility gap in the liquid state of aggregation, compound A is a solvent for the at least one polymer, and compound B raises the phase separation temperature of a solution consisting of the at least one polymer and compound A, b) rendering the solution to form a shaped object, with first and second surfaces, in a die having a temperature above the critical demixing temperature, c) cooling of the shaped object at such a rate that a thermodynamic non-equilibrium liquid-liquid phase separation is initiated and solidification subsequently occurs, d) removal of compounds A and B from the shaped object in order to obtain the membrane from the shaped object, characterized in that compounds A and B are selected such that the boiling point of compound A is at least 50° C. higher than that of compound B and that the solvent system consisting of compounds A and B has a viscosity at room temperature of less than 60 mPa s and that at least one of the surfaces of the shaped object, after it exits the die and before cooling, is subjected to an atmosphere that promotes the evaporation of compound B.

Surprisingly, it has been shown that, by adhering to these process conditions, membranes are obtained in which at least one surface is formed as a separation layer having a dense or at most nanoporous structure and covers the sponge-like, open-pored, microporous structure serving as a support layer. The separation layer is responsible in this case that the membranes produced in accordance with the process of the invention are impervious over long periods of time to breakthrough, in particular of blood plasma. The support layer in this case has a high volume porosity, resulting at the same time in high gas transfer performance for these membranes.

The object is further met by an integrally asymmetrical membrane of the invention, characterized in that the pores, if any, in the separation layer have an average diameter of <100 nm, that the support layer is free of macrovoids and the pores in the support layer are on average substantially isotropic, and that the membrane has a porosity in the range from greater than 50% to less than 75% by volume.

Within the context of the present invention, an integrally asymmetrical membrane is understood to be one in which the separation and support layers consist of the same material, both layers are joined as an integral unit, and are formed together directly during membrane production. In the transition from the separation layer to the support layer, there is a change merely with respect to the membrane structure. Contrasting with this are composite membranes, for example, which have a multilayer structure formed by applying, in a separate process step, a dense layer as a separation layer on a porous, often microporous support layer or support membrane. The result is that the materials constituting the support and separation layers also have different properties in the case of composite membranes.

The average diameter of the pores in the separation layer is understood to be the average of the diameters of the pores in the surface that is formed as a separation layer, whereby a scanning electron microscope image at 60000× magnification is used as a basis.

For compound A, compounds are to be used in which the at least one polymer when heated at most to the boiling point of this compound is dissolved completely to form a homogeneous solution. For this reason, compound A is also referred to as a solvent. To determine the dissolving behaviour of a compound A, it is practical to study the dissolving behaviour with up to 10% polymer by weight, since at higher concentrations a reliable assessment is not possible due to the high viscosities that occur.

In a particularly preferred embodiment of the process of the invention, the at least one polymer and compound A form a binary system that in the liquid state of aggregation has a range in which the system is present as a homogeneous solution and one in which it has a miscibility gap.

For compound B, a compound can be used that dissolves the at least one polymer, but whose dissolving temperature with respect to the at least one polymer is at least 50° C., preferably 100° C. higher than the dissolving temperature of compound A with respect to the at least one polymer. Preferably, however, a non-solvent for the at least one polymer is used for compound B. Non-solvent for the at least one polymer is understood to mean a compound B that does not dissolve the at least one polymer to form a homogeneous solution when heated to at most the boiling point of compound B. Especially preferred are compounds in which the polymer is fully insoluble under the stated conditions or is only partly swollen. As the swelling agent, compound B is taken up noticeably by the polymer but does not lead to formation of a single phase. As a non-solvent, on the other hand, it is not, or only slightly, taken up by the polymer even at higher temperatures.

As previously noted, the at least one polymer and-compound A preferably form a binary system, which in the liquid state of aggregation has a range in which the system is present as a homogeneous solution and one in which it exhibits a miscibility gap. If such a system is cooled from the range in which it is present as a homogenous solution, liquid-liquid demixing initially takes place, whereby in a state of equilibrium two liquid phases coexist, namely one with a high polymer content and the other with a low polymer content. On further cooling, the resultant high-polymer-content phase solidifies. The cooling rate thereby has an influence on the pore structure being created. If the cooling rate is high enough that the liquid-liquid phase separation cannot take place under thermodynamic equilibrium conditions, but still relatively slowly, the liquid-liquid phase separation occurs approximately concurrently with the formation of a large number of droplets of liquid that are of essentially the same size. The resulting polymer object has a cellular microstructure. If the cooling rate is significantly higher, the polymer solidifies before most of the droplets of liquid can form. In this case, non-cellular or even network-like microstructures are formed. The variety of microporous structures formed via processes with liquid-liquid phase separation are described in detail in DE-A-27 37 745.

The employed combinations of polymer, compound A, and compound B, whereby compounds A and B together form the solvent or solvent system, must be convertible jointly into a single homogeneous liquid phase and have an upper critical demixing temperature below which a phase separation into two liquid phases occurs. This is higher, however, than the phase separation temperature of a solution containing equal parts of polymer but only compound A as a solvent. In polymer/compound A systems with a miscibility gap in the liquid state of aggregation, the addition of compound B raises the critical demixing temperature $T_c$. For polymer/compound A systems having no miscibility gap in the liquid state of aggregation, a system must then be created by adding compound B, whereby the system has a miscibility gap in the liquid state of aggregation. Adding compound B enables control of pore size and volume of the porous structures obtained.

Compound A can also be blended with one or more liquids, in particular other solvents. Compound B can also be employed as a mixture with one or more other compounds.

The fraction of polymer and the ratio of compound A to compound B in the solvent system can be determined by generating phase diagrams in simple experiments. Such phase diagrams can be developed using known methods, such as is described in C. A. Smolders, J. J. van Aartsen, A. Steenbergen, Kolloid-Zeitschrift and Zeitschrift fur Polymere, 243 (1971), pp. 14–20.

The polymer component can consist of a single polyolefin or a mixture of several polyolefins. Mixtures of various polyolefins are interesting in that various properties such as permeability or mechanical characteristics can be optimized. For example, by adding just slight amounts of a polyolefin with an ultrahigh molecular weight, for example exceeding $10^6$ Dalton, a strong influence can be exerted on the mechanical properties. A prerequisite for this, of course, is that the polyolefins employed be soluble in the solvent system used.

In an advantageous embodiment of the process of the invention, the at least one polymer is a polyolefin consisting exclusively of carbon and hydrogen. Especially preferred polyolefins are polypropylene and poly(4-methyl-1-pentene) or mixtures of these polyolefins among themselves or with other polyolefins. Of particular advantage is the use of poly(4-methyl-1-pentene) or a mixture of poly(4-methyl-1-pentene) with polypropylene. High gas transfer rates can be realized with good mechanical properties for the membranes. For compounds A and B, which jointly form the solvent system, compounds can be used that fulfill the stated conditions. When using poly(4-methyl-1-pentene) and/or polypropylene as the polymer component, dioctyl adipate and glycerin triacetate are especially suited as compounds A and B, respectively.

The polymer fraction of the mixture from which the solution is formed is preferably 30–60% by weight, and the fraction of the solvent system, consisting of compounds A and B, is 70–40% by weight. The polymer fraction is especially preferred to be 35–50% by weight and the fraction of compounds A and B 65–50% by weight. If necessary, additional substances such as antioxidant agents, nucleating agents, fillers, components to improve biocompatibility, i.e., blood tolerance when using the membrane in oxygenation, such as vitamin E, and similar substances, can be employed as additives to the polymer component, compounds A and B, or to the polymer solution.

The polymer solution formed from the polymer component and the solvent system is given shape using suitable shaping tools, i.e., dies, to produce membranes preferably in flat form or as hollow fiber membranes. Conventional shaping tools such as sheeting, profiled, annular, or hollow-fiber dies can be employed.

In accordance with the invention, at least one of the surfaces of the shaped object leaving the die, i.e., the polymer solution leaving the die in a shaped state, is subjected to a gaseous atmosphere promoting evaporation of compound B before the object is cooled. At the same time, it is advantageous that a continuous exchange of gaseous atmosphere occurs, so that there is no enrichment of compound B in the atmosphere, which at least reduces further evaporation of compound B. Preferably, air is used to form the gaseous atmosphere. Likewise preferred are nitrogen or other inert gases or also media in vapor form. The gaseous atmosphere is advantageously conditioned and preferably has a temperature equal to that of the die.

To evaporate a sufficient fraction of compound B, at least one of the surfaces of the shaped object is subjected to the gaseous atmosphere preferably for at least 0.5 ms.

It is necessary for the process of the invention that the boiling point of compound A be at least 50° C., preferably at least 100° C. higher than that of compound B. It is advantageous for the die temperature not to be substantially lower than the boiling point of compound B, but on the other hand not significantly higher, in order to avoid evaporation of compound B in the die. Therefore, the die temperature is preferably set such that the difference of the boiling point of compound B and the die temperature is between −10° C. and +70° C., especially preferred between 0° C. and 40° C., whereby the die temperature at the same time is above the critical demixing temperature of the polymer solution.

It is assumed that, when carrying out the process of the invention, an evaporation preferably results in the region of the gaseous atmosphere, at the surface subjected to the gaseous atmosphere, of at least a portion of compound B from the surface and the adjacent area of the shaped object in the vicinity of the surface, whereas compound A essentially remains in the shaped object due to the higher boiling point. The result is that on this surface, or in the vicinity of the surface, the fraction of compound B in the polymer solution decreases significantly, and thus the fraction of compound A increases, i.e., enrichment of the solvent takes place at that point. With a high fraction of solvent, however, phase separation is so slow during cooling, or on cooling is no longer possible prior to solidification, that the formation of a low-polymer-content phase leading to pore formation after extraction of the solvent system is insufficient or no longer possible.

In the layer of the shaped polymer solution adjacent to the gaseous atmosphere, referred to in the following as the exterior layer, therefore, no or only slight phase separation into phases with high and low solvent content, respectively, occurs. Regions of the phase with high solvent content, which result in pores during later extraction of the solvent system, are therefore at least substantially lacking in the exterior layer, i.e., the exterior layer is at least substantially pore-free. This layer represents in the context of the invention a separation layer with a denser structure, whereby, when conducting the process of the invention, very thin separation layers can be realized, whose structure can be adjusted from a dense structure to a nanoporous structure with pores smaller than 100 nm. A dense structure is understood to be one for which no pores are detectable under scanning electron microscope examination at 60000× magnification. In individual cases, the formation of the separation layer can also be influenced by drawing the shaped polymer solution after exiting the die, i.e., in the air gap.

In the region of the shaped polymer solution adjacent to the exterior layer, later to be the separation layer, on the other hand, when conducting the process of the invention, a liquid-liquid phase separation takes place, which leads to the formation of a sponge-like, open-pored, microporous structure, i.e., to formation of the support layer. The pore size and porosity of the support layer can be adjusted over a wide range by the composition of the solvent system comprising compounds A and B, whereby porosity values of greater than 50% by volume can readily be attained.

In light of the processes in the phase separation, it is moreover required for the invention that the viscosity of the solvent system be low. For this reason, the viscosity of the mixture of compound A with compound B, forming the solvent system, is lower than 60 mPa s at room temperature. Compounds A and B preferably have a viscosity less than 50 mPa s at room temperature.

If the conditions imposed by the invention with respect to the properties of compounds A and B as well as to the die temperature are not adhered to, this has a negative influence on the structure of the membrane obtained.

For example, in the case that the compounds A and B used have excessive viscosity, the separation into phases with high and low solvent fractions proceeds more slowly, since the diffusion of the polymer molecules is restricted by the high viscosity of the solvent system. It is assumed that the result is a less complete phase separation after a specified amount of time available for the phase separation, and only small regions form containing phases with high and low solvent content. In turn, this means that after extraction of compounds A and B, a very dense-pored structure is produced. In such a case, the separation layer with denser structure is followed by a likewise relatively dense support structure with low porosity. At the same time, such membranes exhibit a slow, gradual transition from the separation layer to the support layer, and a relatively thick, compact region is formed, resulting in the transfer rates for these membranes being very low and unsuitable for blood oxygenation, for example.

To provide the gaseous atmosphere promoting the evaporation of compound B, when using for example a cooling medium to cool the shaped object, the die and cooling medium can be spatially separated such that a gap is formed between them that contains the gaseous atmosphere and through which the shaped object passes. A separation layer will later be formed on the surface of the shaped object subjected to the gaseous atmosphere in the gap.

In producing flat membranes, for example, the polymer solution extruded through a sheeting die can, as a flat sheet, be initially passed through a gap, such as one containing air, i.e., an air gap, before being cooled. In this case, both surfaces of the flat sheet, as well as the edges, are enveloped by the gaseous atmosphere, and the resulting flat membrane therefore exhibits a separation layer on both surfaces.

If the extrusion of the flat sheet is performed directly onto a heated carrier, for example in the form of a heating roller, and if the flat sheet on the carrier then passes through a defined section of gaseous atmosphere, only one surface of the flat sheet, namely that opposite the heating roller, comes into contact with the gaseous atmosphere, so that a separation layer can form only on this surface. In this way, a flat membrane is produced having a separation layer on only one of its surfaces.

In the case of hollow-fiber membrane production, the polymer solution is extruded through the annular gap of the corresponding hollow-fiber die to form a shaped object, i.e., a hollow fiber. A fluid is extruded through the central bore of the hollow-fiber die that acts as an interior filler that shapes and stabilizes the lumen of the hollow-fiber membrane. During extrusion, the interior filler is brought to essentially the same temperature as the polymer solution. The extruded hollow fiber or resulting hollow-fiber membrane then exhibits a surface toward the lumen, the interior surface, and a surface opposite the lumen, the exterior surface, separated from the interior surface by the wall of the hollow fiber or hollow-fiber membrane.

The hollow fiber leaving the die can likewise be led through a gap formed between the die and cooling medium and containing the gaseous atmosphere. This results in the exterior surface of the hollow fiber coming into contact with the gaseous atmosphere promoting the evaporation of compound B, and the resulting hollow-fiber membrane then has a separation layer on its exterior surface.

The interior filler employed in extrusion of the hollow fiber can be in gaseous or liquid form. When using a liquid as the interior filler, a liquid must be selected that essentially does not dissolve the polymer or polymers in the shaped polymer solution below the critical demixing temperature of the polymer solution. Otherwise, the same liquids can be employed that are also used as cooling media. The interior filler also preferably contains compounds A and B and especially preferably also in the same ratio of compound A to compound B as the solvent system of the polymer solution. In this case, the exterior surface of the hollow fiber must be subjected to a gaseous atmosphere promoting the evaporation of compound B, such as in a corresponding gap, so that the resulting hollow fiber membrane has a separation layer.

If the fluid is gaseous, it can be air, a vaporous substance, or preferably nitrogen.

In the preferred case of using a gaseous interior filler, the filler can at the same time be a gaseous atmosphere promoting the evaporation of compound B. In this case, air, nitrogen, other inert gases, or also vaporous media can be used as the interior filler. When using such an interior filler that simultaneously serves as a gaseous atmosphere promoting evaporation of compound B, formation of a separation layer can result on the interior surface of the hollow fiber. In an individual case, however, it can happen that rapid saturation of the gaseous interior filler with vaporous compound B is attained, thus leaving an amount of evaporated compound B that is insufficient to form a separation layer. In this case, the interior surface of the hollow-fiber membrane has no separation layer.

If the amount of evaporated compound B is sufficient to form a separation layer on the interior surface, and if in such a case the exterior surface of the hollow fiber is not subjected to an atmosphere promoting the evaporation of compound B, such as an atmosphere saturated with compound B, no separation layer can form on the exterior surface. A hollow-fiber membrane is thereby produced having a separation layer only on its interior surface.

After at least one of the surfaces of the shaped object has been subjected to a gaseous atmosphere promoting the evaporation of compound B, it is cooled, so that a thermodynamic non-equilibrium liquid-liquid phase separation occurs in the shaped object, i.e., in the shaped polymer solution, and the polymer structure subsequently solidifies and hardens.

Preferably, cooling occurs in a cooling medium. For example, in the case of producing flat membranes, the shaped flat sheet can also be laid onto an appropriately temperature controlled or cooled cooling roller for the cooling process. The cooling medium employed can be gaseous or liquid. Liquid cooling media are preferred, however. To initiate a thermodynamic non-equilibrium liquid-liquid phase separation, the temperature of the cooling medium must be below the critical demixing temperature or phase separation temperature of the polymer solution used. The cooling medium preferably has a temperature at least 100° C. below the phase separation temperature. It is also possible for cooling to take place stepwise.

There are no particular demands placed on the composition of the cooling medium, as long as the cooling medium is inert with respect to the polymer or polymers, i.e., does not substantially dissolve the latter below the critical demixing temperature of the polymer solution. The cooling medium can be miscible with the solvent system or inert with respect to the solvent system. Advantageously, the cooling medium contains compound A. Especially preferred, however, is a cooling medium consisting of compounds A and B present in the solvent system and, in a further especially preferred embodiment, having the same ratio of compound A to compound B as the solvent system.

The cooling medium is preferably in a shaft or spinning tube which the shaped object passes through for cooling purposes. The cooling medium and shaped object are generally fed in the same direction through the shaft or spinning tube. The shaped object and cooling medium can be fed at the same or different linear speeds through the spinning tube, whereby, depending on the requirement, either the shaped object or the cooling medium can have the higher linear speed. Such process variants are described in DE-A-28 33 493 or EP-A-133 882, for example.

After cooling and hardening of the polymer structure, compounds A and B are removed from the shaped object, resulting in formation of the membrane. Removal can be performed, for example, by extraction. Preferably, extraction agents are used that do not dissolve the polymer or polymers but are miscible with compounds A and B. Subsequent drying at elevated temperatures can be necessary to remove the extraction agent from the membrane.

Before or after the removal of at least a substantial portion of the solvent system, a slight drawing of the membrane can take place in order in particular to modify the properties of the separation layer in a specific manner. The pore size of the separation layer can be adapted to that required for the particular membrane application. For example, a dense separation layer can be opened up by the drawing process, so that pores result in the separation layer. The pores, however, should not be too large and, in accordance with the invention, not exceed 100 nm, so that the membrane is suitable for gas exchange and breakthrough of liquid can be avoided. For this reason, the drawing should generally not exceed 10%. The drawing can, as required, also be performed in multiple directions and is preferably performed at elevated temperatures. For example, such drawing can also be conducted during drying of the membrane that might be necessary after extraction.

The process of the invention is particularly suited to producing the integrally asymmetrical membrane for gas exchange of the invention.

Due to its structure, the membrane of the invention is distinguished by high gas transfer rates with simultaneous high levels of safety with respect to a breakthrough of the liquid, from which, when using the membrane of the invention, a gaseous component is separated or to which a gaseous component is added, and also by good mechanical properties. It is required in this case that the membrane have a high volume porosity, whereby the latter is defined substantially by the structure of the support layer, and a defined dense or nanoporous separation layer with reduced thickness.

The support layer of the membrane of the invention can have various structures. It can have a cellular structure, in which the pores can be described as enveloped microcells that are interconnected by channels, smaller pores, or passages. It can also have a non-cellular structure, in which the polymer phase and the pores form interpenetrating network structures. In any case, however, the support layer is free of macrovoids, i.e., free of such pores often referred to in the literature as finger pores or caverns.

The pores of the support layer can have any geometry and be, for example, of longitudinal, cylindrical, or rounded form, or also have a more or less irregular form. In accordance with the invention, the pores in the support layer are on average essentially isotropic. This is understood to mean that, although the individual pores can also have an elongated shape, the pores on average in all spatial directions have essentially the same extension, whereby deviations between the extensions in the individual spatial directions are less than or equal to 20%.

With an insufficiently low volume porosity, i.e., an insufficient pore fraction compared to the total volume of the membrane, the attainable gas transfer rates are too low. On the other hand, an excessive pore fraction in the membrane leads to deficient mechanical properties, and the membrane cannot be readily processed in subsequent processing steps. For this reason, the membrane of the invention preferably has a volume porosity in the range of greater than 50% to less than 75% by volume, preferably in the range of greater than 50% to less than 65% by volume.

The membrane of the invention can have a separation layer on only one of its surfaces, or it can have a separation layer on both surfaces. The separation layer influences on the one hand the transfer rates but on the other hand the breakthrough time, i.e., the time it is secure against a breakthrough of the liquid from which, in accordance with the invention, a gaseous component is to be separated or to which a gaseous component is to be added, or against a breakthrough of components contained in the liquid. With a dense separation layer, very long breakthrough times are the result, but the transfer rates are limited, since in dense membrane layers the gas transfer takes place solely via a comparatively slow solution diffusion, in contrast to the considerably greater Knudsen flow in porous structures. In the case of a nanoporous separation layer, on the other hand, the gas transfer rates are higher than those with a dense separation layer, but reduced breakthrough times may result due to the pores.

In a preferred embodiment of the membrane of the invention, the at least one separation layer is dense. In a further preferred embodiment the at least one separation layer has pores with an average diameter between 10 nm and 100 nm. Here, the separation layer must not be too thin, since this increases the risk of defects and thus of breakthrough. However, the time to actual breakthrough is relatively long, since with the membranes of the invention there is no preferred direction for the flow of a liquid; rather, the course of the liquid is tortuous due to the pore structure. In contrast, the membranes produced according to the mentioned melt-drawing process have to be discerned, in which, due to the pronounced anisotropy of the pores, a preferred direction for the flow of the liquids from one surface to another results.

While excessively thin separation layers make the risk of defects unacceptably high, an excessive separation layer thickness makes the transfer rates too low. Preferably, therefore, the thickness of the separation layer lies between 0.1 $\mu$m and 1 $\mu$m, especially preferably between 0.1 $\mu$m and 0.6 $\mu$m. The thickness of the separation layer can be determined for the membranes of the invention in a simple manner using fracture images generated by scanning electronic microscopy or by ultrathin-section characterizations using transmission electron microscopy.

An important application of the membrane of the invention is oxygenation of blood. In these applications, as previously noted, the time in which the membrane is stable against a breakthrough of blood plasma, i.e., the plasma breakthrough time, plays a role. It must be emphasized that plasma breakthrough is a considerably more complex process than the mere penetration of a hydrophobic membrane by a hydrophilic liquid. According to accepted opinion, plasma breakthrough is induced by the fact that initially phospholipids in the blood effect a hydrophilation of the pore system of the membrane, and in a subsequent step a sudden penetration of blood plasma into the hydrophilated pore system takes place. The critical variable for a liquid breakthrough is therefore seen as the plasma breakthrough time. The membranes of the invention preferably exhibit a plasma breakthrough time of at least 20 hours, and especially preferably a plasma breakthrough time of at least 48 hours.

Despite the presence of a separation layer with denser structure, the membrane of the invention exhibits high gas transfer rates, which are comparable to or even higher than those of conventional membranes for gas transfer without such a separation layer. The $O_2$ and $CO_2$ transfer rates are regarded as a measure for the gas transfer capacity of the membrane, in each case with respect to water as the gas-absorbing or releasing fluid. Preferably, the membrane of the invention has an $O_2$ transfer rate of >140 ml/(min*m$^2$) and a $CO_2$ transfer rate of >1900 ml/(min*m$^2$) and especially preferably an $O_2$ transfer rate of >190 ml/(min*m$^2$) and a $CO_2$ transfer rate of >2200 ml/(min*m$^2$).

In a preferred embodiment of the membrane of the invention, the membrane structure changes abruptly in the transition from the separation layer to the support layer, i.e., the membrane structure changes substantially transition-free and abruptly from the microporous support structure to the separation layer. In comparison to membranes with a gradual transition from the separation layer to the support layer, membranes with such a structure have the advantage of higher permeability of the support layer for gases to be transferred, since the support layer is less compact in the area adjacent to the separation layer.

The hydrophobic membrane of the invention consists primarily of at least one polymer selected from the group of polyolefins. The at least one polymer can be a single polyolefin or a mixture of several polyolefins. Mixtures of polyolefins with various molecular weights or various polyolefins are interesting to the extent that various properties can be optimized, such as gas transfer rates or mechanical properties. For example, by adding just slight amounts of a polyolefin with an ultrahigh molecular weight, exceeding $10^6$ Dalton, for example, a strong influence can be exerted on the mechanical properties.

Preferably, the membrane of the invention is composed of a polyolefin consisting exclusively of carbon and hydrogen. Especially preferred polyolefins are polypropylene and poly(4-methyl-1-pentene) or a mixture of these polyoletins with other polyolefins. Of particular advantage is the use of poly(4-methyl-1-pentene) or a mixture of poly(4-methyl-1-pentene) with polypropylene. High gas transfer rates can be realized with good mechanical properties for the membrane. If necessary, the at least one polymer can contain additives such as antioxidant agents, nucleating agents, fillers, components to improve biocompatibility, i.e., blood tolerance when using membrane in oxygenation, such as vitamin E, and similar substances.

In a preferred embodiment, the membrane is a flat membrane. The flat membrane preferably has a thickness between 10 and 300 μm, especially preferably between 50 and 150 μm. The flat membrane can have a separation layer on only one of its surfaces or on both surfaces.

In a likewise preferred embodiment, the membrane of the invention is a hollow-fiber membrane. Depending on the embodiment, it can have a separation layer on its interior surface only, i.e., on the surface toward the lumen, or only on its exterior surface, i.e., the surface opposite the lumen, or on both the interior and exterior surfaces. The hollow fiber membrane preferably has a diameter between 10 and 500 μm, especially preferably between 100 and 300 μm. A wall thickness of the hollow fiber membrane between 5 and 150 μm is advantageous, and is a thickness between 10 and 100 μm is especially advantageous.

The membrane of the invention has outstanding mechanical properties, readily enabling further processing in subsequent processing steps. For example, when using the hollow-fiber membrane, it has proven beneficial with respect to the performance characteristics of membrane modules made therefrom for the hollow fiber membranes to be initially constructed by appropriate knitting processes, for example, into mats of hollow fiber membranes essentially parallel to each other, which are then fashioned into bundles. The associated textile processes impose stringent demands on the mechanical properties of the membrane, in particular on the tensile strength and elongation. These requirements are fulfilled by the membrane of the invention. The hollow fiber membranes of the invention preferably have a breaking force of at least 70 cN and an elongation at break of at least 75%.

The membranes of the invention can be used in numerous applications in which a membrane is required with a dense or nanoporous separation layer. Preferably, the membrane of the invention is suited for applications in the field of gas exchange, in which gaseous components are to be separated from liquids or added to them. Due to the high impermeability to plasma, i.e., to the long plasma breakthrough times, and the high gas transfer capacity for $O_2$ and $CO_2$, the membranes of the invention are excellently suited for use in oxygenators, i.e., for the oxygenation of blood and in particular for the extended-duration oxygenation of blood.

The invention will now be described in more detail with reference to the following examples.

In the examples, the following methods were employed to characterize the membranes obtained:

Determination of the Plasma Breakthrough Time

To determine the plasma breakthrough time, a phospholipid solution maintained at 37° C. (1.5 g L-a-Phosphatidy-LCholine in 500 ml physiological saline solution) is allowed to flow at 6 l/(min*m$^2$) and a pressure of 1.0 bar across one surface of a membrane sample. Air is allowed to flow along the other surface of the membrane sample, the air after exiting the membrane sample being fed through a cooling trap. The weight of the liquid accumulated in the cooling trap is measured as a function of time. The time to occurrence of a significant increase in the weight, i.e., to the first significant accumulation of liquid in the cooling trap, is designated as the plasma breakthrough time.

Determination of the $O_2$ and $CO_2$ Transfer Rates

To determine the $O_2$ and $CO_2$ transfer rates, water enriched with $CO_2$ to bring the conductivity to 40 μS/cm is directed at 24° C. along one surface of the membrane sample. The flow velocity of the water along the membrane surface is adjusted such that an increase of the rate does not substantially influence the determined transfer rates. $O_2$ is allowed to flow on the other surface of the membrane sample. This removes $CO_2$ from the water and adds $O_2$ to it. The change in the $CO_2$ concentration of the water is observed by conductivity measurement. Using an empirical equation determined on the basis of calibration tests with water samples of different known $CO_2$ concentrations, the conductivity values L are converted to the respective $CO_2$ concentrations c using the formula $$c(CO_2)[ml/l]=0.1702*L^2[\mu S/cm].$$

To measure the $O_2$ concentration, a membrane-covered amperometric oxygen sensor with potentiostatic three-electrode system is used.

Determination of Volume Porosity

The volume porosity test is conducted based on the process described in ASTM D 4197-82, test method B. A liquid that does not wet the membrane material is pressed into the pore system of a membrane sample, and the volume of the penetrated liquid determined. The volume porosity of the membrane is then calculated as the ratio of this volume to the total volume of the membrane sample.

Determination of the Breaking Force and Elongation at Break

To characterize the membrane with respect to its breaking force and elongation at break, the membrane is elongated at room temperature at constant rate until it breaks, and the force required therefor is determined along with the change in length.

Determination of the Surface Porosity

The surface porosity is determined using scanning electron microscope (SEM) images. An SEM image, taken at 10000× magnification, of a section of the membrane surface measuring 8.3 μm×6.2 μm is subjected to image analysis. The SEM image is digitized and the area of the dark pores standing out against the light-colored membrane material is determined by computer. The surface porosity is then calculated as the ratio of the pore area to the total area.

Determination of the Average Diameter of the Pores in the Separation Layer

The determination of the average diameter of the pores in the separation layer is performed in a manner analogous to determining the surface porosity using an image analysis process. The pores are assumed to have a circular cross-section. The average pore diameter is then the arithmetic mean of all visible pores on a membrane surface of approx. 8 μm×6 μm at 60000× magnification.

EXAMPLE 1

At 260° C., a solution was prepared of 40% by weight poly(4-methyl-1-pentene) and 60% by weight of a mixture of 65% by weight dioctyl adipate (compound A) and 36% by weight glycerin triacetate (compound B) as the solvent system. The boiling points and viscosities of these two compounds are given in Table 1.

TABLE 1

| Compound | Boiling point [° C.] | Viscosity (room temperature) [mPa s] |
|---|---|---|
| Dioctyl adipate (A) | 390 | 14.7 |
| Glycerin triacetate (B) | 258 | 23 |

This solution was extruded through a hollow-fiber die with an annular gap of 0.3 mm and formed into hollow fibers. Nitrogen was used as the interior filler. The die had a temperature of 240° C. After an air section of ca. 5 mm, the hollow fibers passed through a 2 m long spinning tube through which flowed a cooling medium maintained at 18° C. A mixture of 65% by weight dioctyl adipate and 35% by weight glycerin triacetate was used as the cooling medium. The flow rate of the cooling medium was adapted to the spinning speed and was approx. 90 m/min. As a result of the cooling in the spinning tube, phase separation and solidification of the hollow fibers occurred, so that the latter could be drawn continuously from the spinning tube. The hollow fibers were then extracted in isopropanol for 6 hours at 60° C. to remove the solvent system, and the hollow fiber membranes thus obtained were subsequently dried for 6 sec. at 120° C. During drying, drawing by approx. 5% was conducted.

Figure 1:
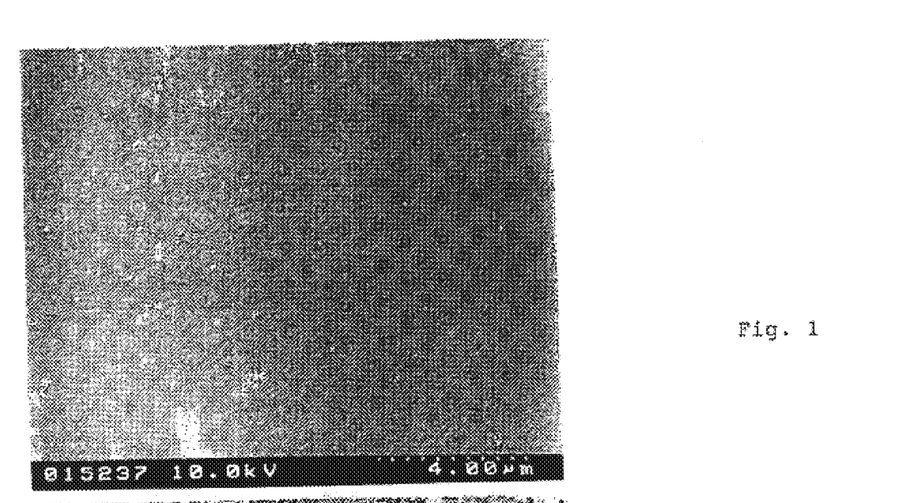
FIG. 1: shows a scanning electron microscopic (SEM) image of the exterior surface of a hollow fiber membrane of example 1 at 6750×magnification.
Figure 2:
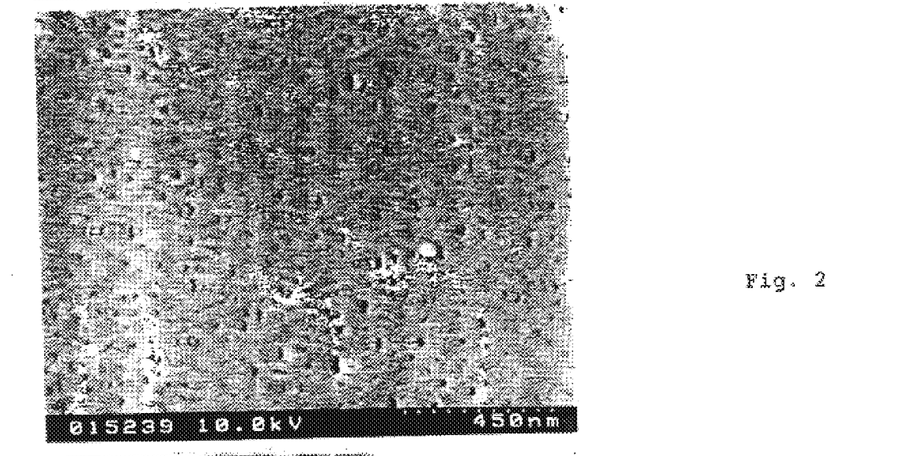
FIG. 2: SEM image of the exterior surface of a hollow-fiber membrane of example 1 at 60000× magnification.
Figure 3:
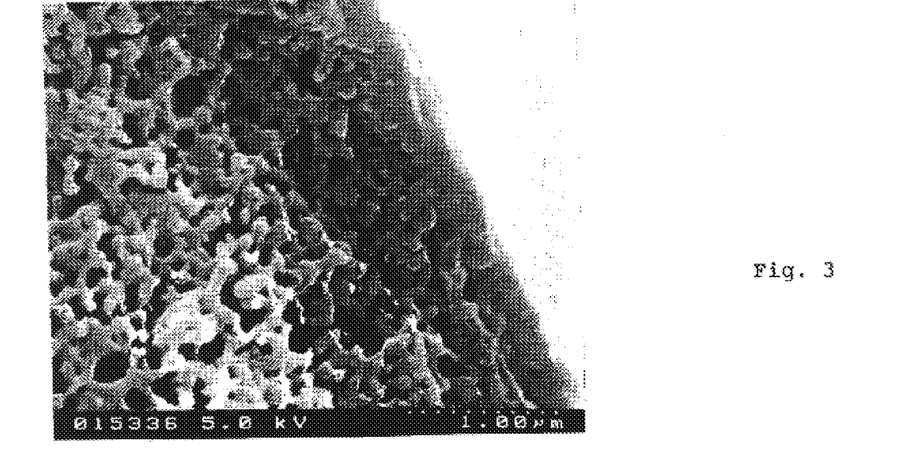
FIG. 3: SEM image of the surface of fracture perpendicular to the longitudinal axis of a hollow-fiber membrane of example 1 at 27000× magnification.

The properties of the hollow fiber membranes obtained are summarized in Table 2. In analysis using the scanning electron microscope (SEM), the exterior surface of the hollow fiber membranes of this example exhibits no detectable pores at a magnification of 6750× (FIG. 1). Only at very high magnification is a uniform porous structure detectable, with pores at most 100 nm in size (FIG. 2). The image of a surface of fracture perpendicular to the longitudinal axis of the hollow-fiber membrane clearly shows the sponge-like, open-pored, microporous support structure, which is followed in the direction of the exterior surface by the nanoporous separation layer, which in this example has a thickness of approx. 0.2 μm (FIG. 3). By virtue of the extremely thin separation layer, the volume porosity of the membranes was not significantly reduced. For the membrane of example 1, the volume porosity is 52.5% by volume. This high volume porosity leads to the high $O_2$ and $CO_2$ transfer rates listed in Table 2. At the same time, with a breaking force of 81 cN and an elongation at break of 101%, the hollow fiber membranes exhibit mechanical properties that permit good processing in subsequent steps.

EXAMPLE 2

Figure 4:
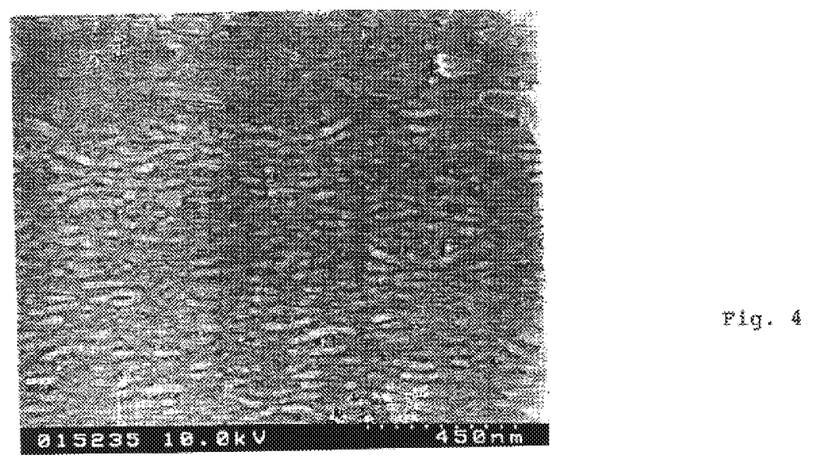
FIG. 4: SEM image of the exterior surface of a hollow-fiber membrane of Example 2 at 60000× magnification.

Hollow fiber membranes were produced according to example 1. Instead of drying at 120° C. in conjunction with drawing, in example 2 drying at room temperature was conducted and the hollow fiber membranes were not drawn. The membranes obtained had the properties listed in Table 2. The separation layer on the exterior surface of the membrane of this example is denser compared to the separation layer of the membrane of example 1: at 60000× magnification, only individual pores with a size of less than 50 nm are detectable in the scanning electron microscopic image (FIG. 4).

Comparative Example 1

A solution was prepared containing 44% by weight polypropylene and 56% by weight of a solvent system consisting of 75% by weight of soybean oil as compound A and 25% by weight of castor oil as compound B. The solution was extruded through a hollow-fiber die at 235° C., and the extruded hollow fiber, after passing an air gap of 5 mm in length, was directed through a spinning tube containing a cooling medium consisting of 75% by weight of soybean oil and 35% by weight of castor oil. The remaining process conditions were those of example 1.

As Table 3 shows, and considering the die temperature of 235° C., the properties of the compounds A and B used in this comparative example and the process conditions do not meet the properties and conditions required by the invention.

TABLE 3

| Compound | Boiling point [° C.] | Viscosity (room temperature) [mPa s] |
|---|---|---|
| Soybean oil (A) | >500(*) | 69 |
| Castor oil (B) | 313 | 950–1100 |

(*)Soybean oil has a boiling point of 308° C. at 0.067 mbar.

Figure 5:
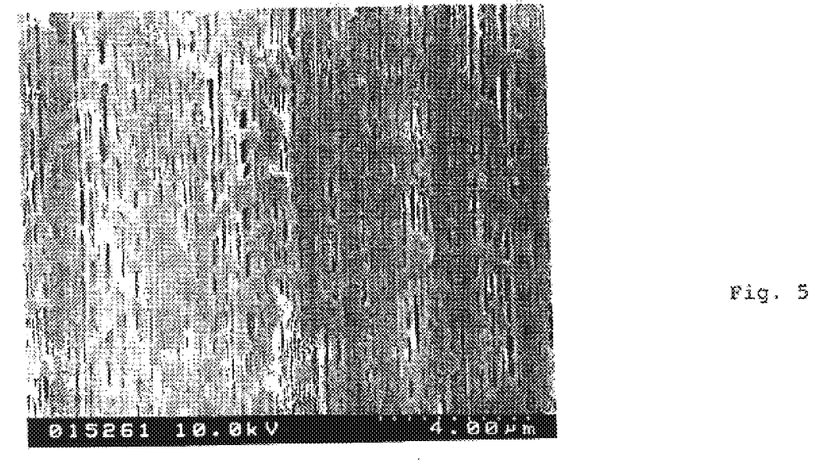
FIG. 5: SEM image of the exterior surface of a hollow-fiber membrane of comparative example 1 at 6750× magnification.

The hollow fiber membranes obtained from this example have an open-pored structure on the exterior surface of the membrane as well, which during production was positioned toward the air gap. This is evident from the SEM image in FIG. 5, in which numerous pores with size exceeding 0.1 μm can be seen in the exterior surface. The open-pored structure is a result of the selection of the compounds A and B constituting the solvent system, the selection not being in accordance with the invention. As a result, the 3–5 hour plasma breakthrough times for the membranes of this comparative example are short, and the membranes are therefore not suited to extended use.

At the same time, the hollow fiber membranes of this comparative example have only a small volume porosity of 44.5%, which can be attributed to the high viscosity of the soybean oil and castor oil used as compounds in the solvent system. The result of this is relatively low transfer rates. The properties of these membranes are also summarized in Table 2. Membranes produced in accordance with this comparative example, however, are usable in conventional blood oxygenation.

EXAMPLE 3

Figure 6:
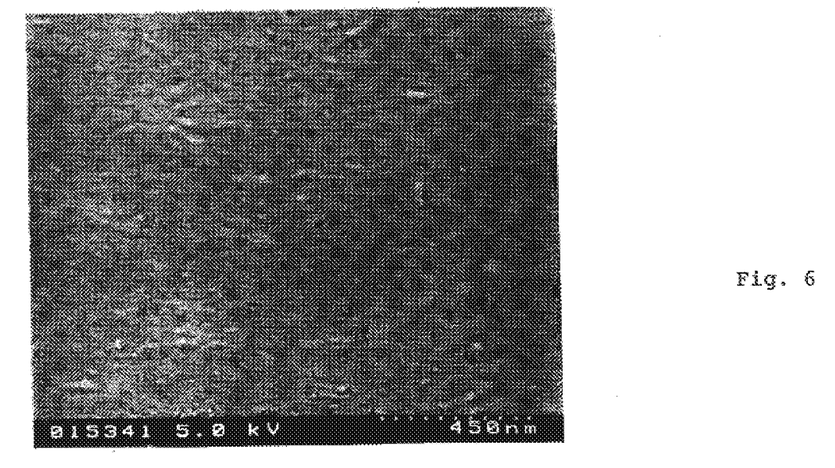
FIG. 6: SEM image of the exterior surface of a hollow-fiber membrane of example 3 at 60000× magnification.

The procedure was the same as for example 1. The solvent system and cooling medium, however, were a mixture of 55% by weight dioctyl adipate and 45% by weight glycerin triacetate. The die temperature was set to 260° C. The hollow fiber membranes thus obtained exhibited the properties listed in Table 2. With this recipe, the tightness of the separation layer can be increased compared to example 1. In the SEM image at 60000× magnification, only isolated pores with a size less than 50 nm (FIG. 6) are recognizable. The transfer rates, however, are not influenced by this, as indicated by Table 2; this might be attributable to the high volume porosity of 58.5% by volume. For these membranes, a plasma breakthrough time of 48.6 hours was determined. The membranes' breaking force and elongation at break were sufficient for good subsequent processing into hollow fiber mats using a knitting process.

EXAMPLE 4

The procedure was the same as in example 1, whereby a solvent system consisting of 60% by weight dioctyl adipate and 40% by weight glycerin triacetate, and a cooling medium consisting of 55% by weight of dioctyl adipate and 45% by weight of glycerin triacetate was used. With this recipe as well, a very high hollow-fiber membrane porosity of 61.9% by volume as well as a further increase in the gas transfer rates compared to the membrane of example 3 were attained, as the results shown in Table 2 indicate. The plasma breakthrough time was determined to be 20.5 hours. The exterior surface of the membranes of this example has structure similar to that of the membranes of example 1.

EXAMPLE 5

Hollow fiber membranes were produced as in example 1. Instead of pure poly(4-methyl-1-pentene), a mixture of 90% by weight poly(4-methyl-1-pentene) and 10% by weight polypropylene was used. The die temperature was likewise 240° C.

Figure 7:
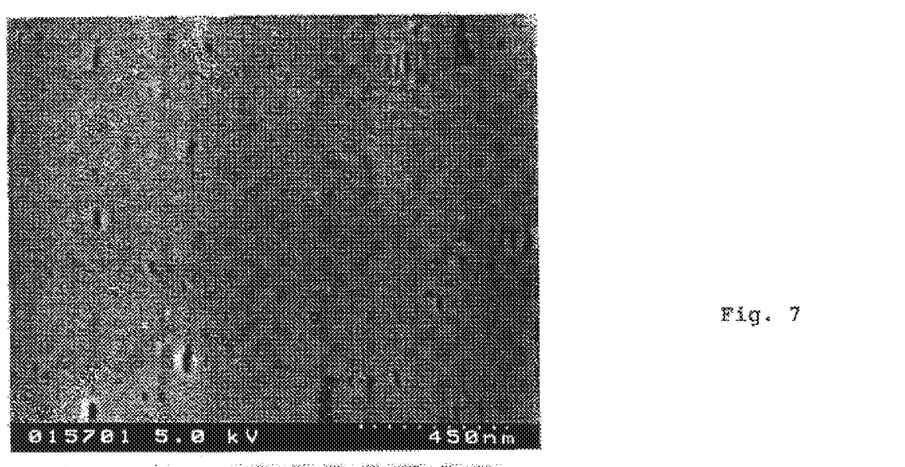
FIG. 7: SEM image of the exterior surface of a hollow-fiber membrane of example 5 at 60000× magnification.
Figure 8:
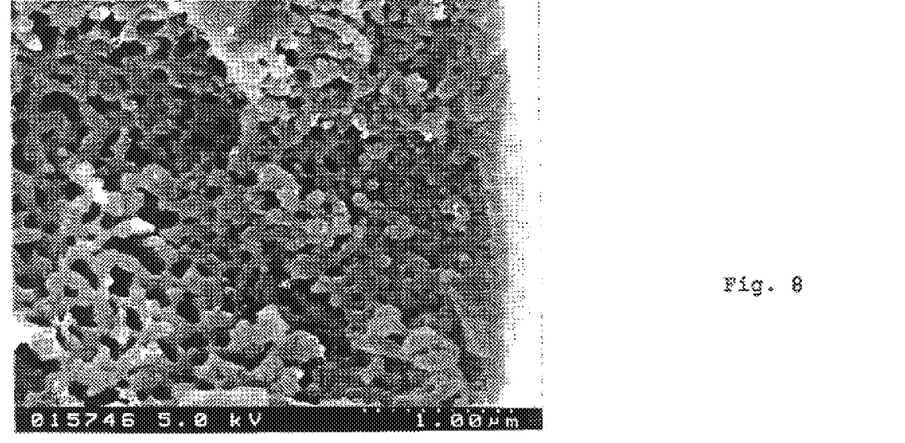
FIG. 8: SEM image of the surface of fracture perpendicular to the longitudinal axis of a hollow-fiber membrane of example 5 with a separation layer on the exterior surface, at 27000× magnification.
Figure 9:
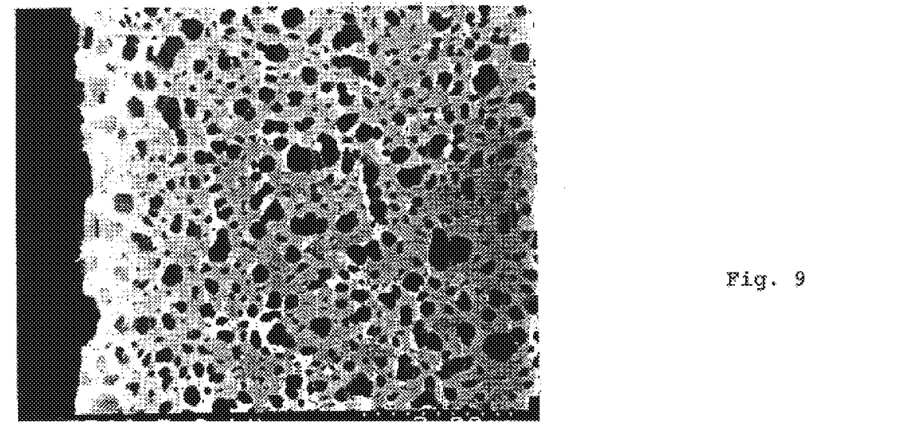
FIG. 9: SEM image of the surface of fracture perpendicular to the longitudinal axis of a hollow-fiber membrane of example 5 with open-pored, microporous interior surface, 13500× magnification.

The properties of the hollow fiber membranes obtained can again be taken from Table 2. In the SEM image of the exterior surface of the membrane (FIG. 7), individual pores can be seen with a size under 100 nm, but the pore density is lower than in example 1, in which pure poly(4-methyl-1-pentene) had been used as a polymer. The characterization of the surface of fraction using SEM indicates that the exterior surface of the membrane has a separation layer approximately 0.1 μm thick (FIG. 8), and the interior of the membrane wall and the interior surface are sponge-like, open-pored, and microporous (FIG. 9).

Compared to the membrane of pure poly(4-methyl-1-pentene) of example 1, the transfer rates are somewhat higher at comparable volume porosity values. Through the addition of polypropylene, furthermore, the elongation at break in particular is higher. The hollow-fiber membranes of this example were excellently suited to further processing into knit hollow-fiber mats.

EXAMPLE 6

The procedure of example 5 was followed. Instead of the polymer mixture used in example 5, however, a mixture of 75% by weight poly(4-methyl-1-pentene) and 25% by weight polypropylene was used. The pore morphology and the properties of the membrane of example 6 were approximately the same as those of membranes of example 5 (see Table 2).

EXAMPLE 7

Hollow-fiber membranes were produced from a solution containing 40% by weight polypropylene and 60% by weight of a mixture of 60% by weight dioctyl adipate and 40% by weight of glycerin triacetate as the solvent system. A mixture of 65% by weight dioctyl adipate and 35% by weight glycerin triacetate served as the cooling medium. Otherwise, the procedure was analogous to example 1.

Figure 10:
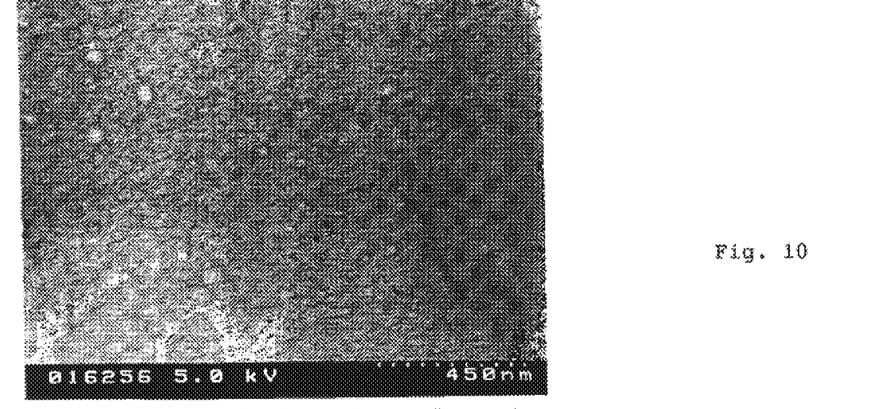
FIG. 10: SEM image of the exterior surface of a hollow-fiber membrane of example 7 at 60000× magnification.
Figure 11:
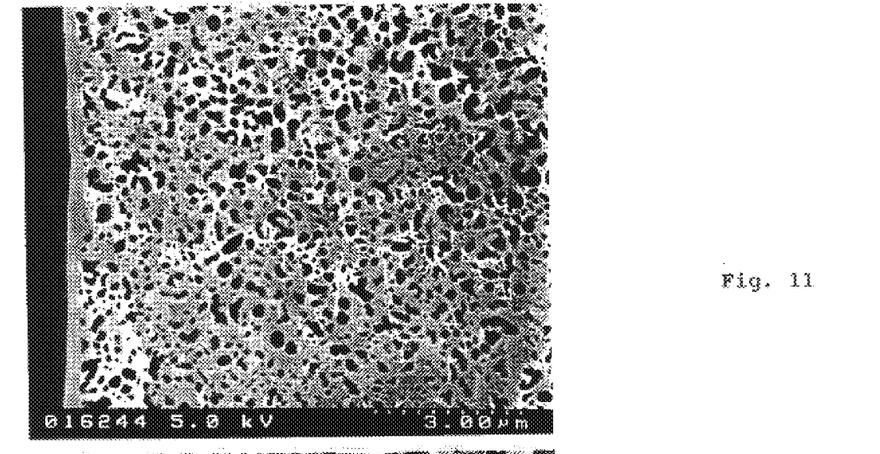
FIG. 11: SEM image of the surface of fracture perpendicular to the longitudinal axis of a hollow-fiber membrane of example 7 with separation layer on the interior surface, at 9000× magnification.
Figure 12:
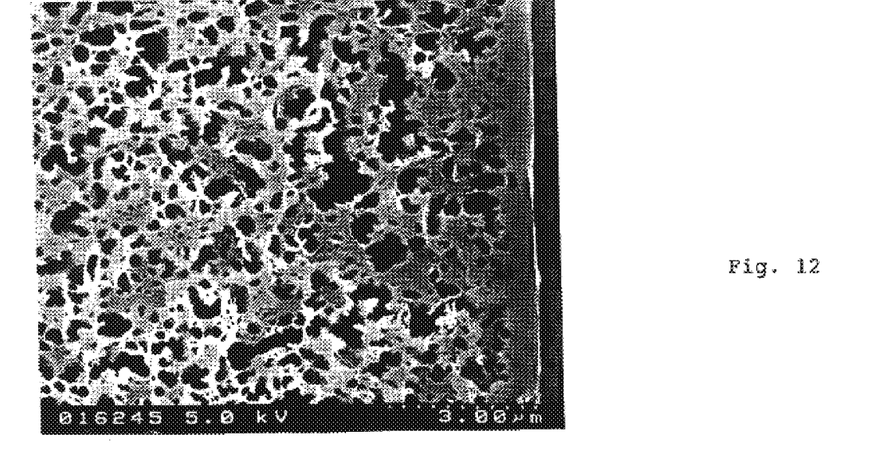
FIG. 12: SEM image of the surface of fracture perpendicular to the longitudinal axis of a hollow-fiber membrane of example 7 with separation layer on the exterior surface, 9000× magnification.
Figure 13:
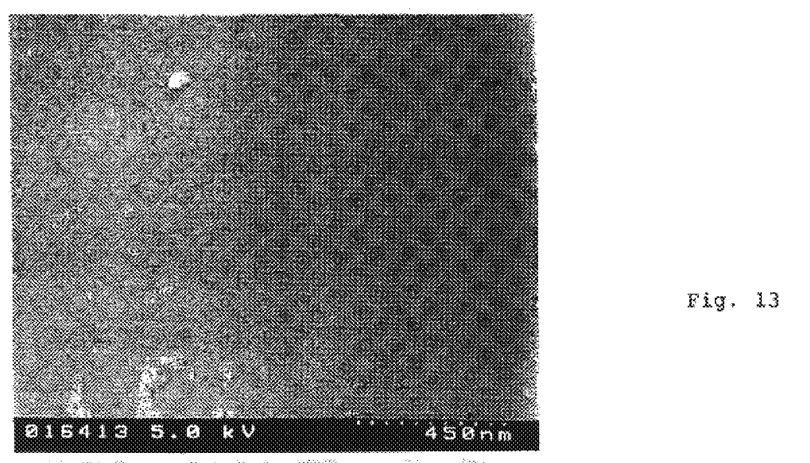
FIG. 13: SEM image of the exterior surface of a hollow-fiber membrane of example 8 at 60000× magnification.

The hollow fiber membranes of this example have a dense interior surface and a dense exterior surface, for which no pores are evident in the SEM image even at 60000× magnification (FIG. 10). From the SEM fracture image analysis of the hollow-fiber membranes of this example, a separation layer on the interior surface (FIG. 11) and one on the exterior surface (FIG. 12) are clearly evident, whereby the transition of the respective separation layer to the support layer is abrupt. The thickness of the separation layer on the exterior surface can be determined as approx. 0.5 μm and that of the separation layer on the interior surface as approx. 0.3 μm. Due to the overall comparatively greater thickness of the separation layer and the generally lower gas permeability of polypropylene compared to poly(4-methyl-1-pentene), the transfer rates of this membrane are in part lower that those of the membranes in previous examples (see Table 2). The plasma breakthrough time of the membrane of this example is significantly greater than 20 hours; the measurement of the plasma breakthrough time, however, had been discontinued after 24 hours.

EXAMPLE 8

The same procedure as in example 5 was followed. However, by selecting a higher extrusion capacity compared to that of example 3, a hollow fiber membrane with a thicker wall was obtained. Through the higher wall thickness, membranes with higher breaking force and elongation at break resulted compared to example 5 (see Table 2), which also meant that drawing of the hollow-fiber membranes during drying was reduced compared to those of example 5. In contrast to the membrane described in example 5 with nanoporous separation layer, a membrane with dense separation layer on the exterior surface is obtained (FIG. 12), which might be attributable to the reduced drawing.

Figure 14:
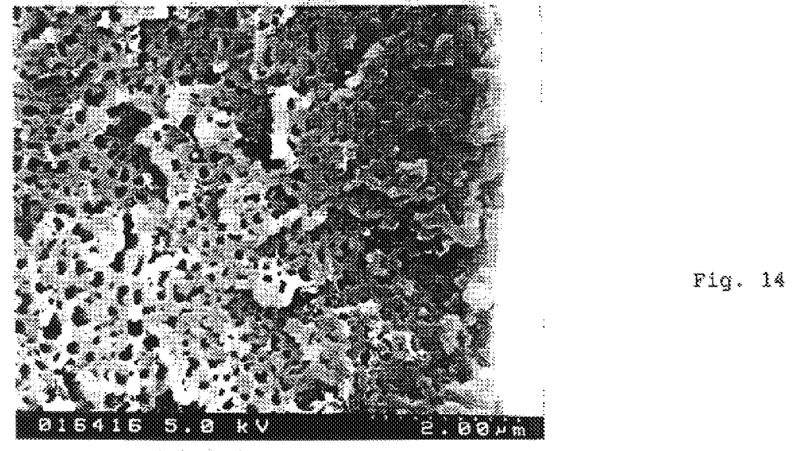
FIG. 14: SEM image of the surface of fracture perpendicular to the longitudinal axis of a hollow-fiber membrane of example 8 with separation layer on the exterior surface, at 13500× magnification.
Figure 15:
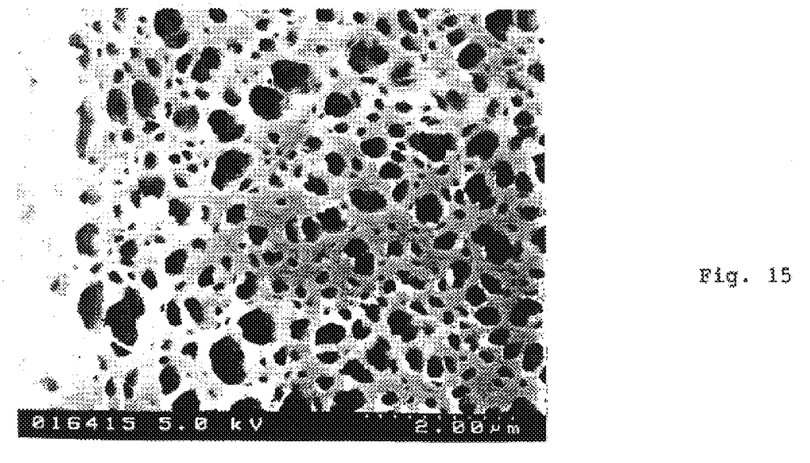
FIG. 15: SEM image of the surface of fracture perpendicular to the longitudinal axis of a hollow-fiber membrane of example 8 with open-pored, microporous interior surface and support structure, at 13500× magnification.

In the fracture image, a separation layer of approx. 0.1–0.2 μm can be detected on the exterior surface of the membrane (FIG. 14), while the interior of the wall and the interior surface are open-pored and microporous (FIG. 15). Despite the large wall thickness, high gas transfer rates are determined for the membranes of this example, which are significantly higher than those of the conventional membranes for oxygenation of comparative example 1 (see Table 2). The plasma breakthrough time of the hollow fiber membranes of this example 8 were determined to be at 75 hours. When this time had been reached, the test was discontinued.

TABLE 2

| Example | Lumen [μm] | Wall thickness [μm] | $O_2$ transfer rate [ml/min*m²] | $CO_2$ transfer rate [ml/min*m²] | Volume porosity [%] | Surface porosity [%] | Elongation at break [%] | Breaking force [cN] | Plasma breakthrough time [hrs.] |
|---|---|---|---|---|---|---|---|---|---|
| 1 | 263 | 49 | 261 | 2505 | 52.5 |  | 101 | 81 |  |
| 2 | 262 | 46 |  |  |  |  |  |  |  |
| 3 | 265 | 50 | 276 | 2357 | 58.5 | 0.70 | 91 | 76 | 48.6 |
| 4 | 251 | 49 | 292 | 2664 | 61.9 | 0.20 | 77 | 70 | 20.5 |
| 5 | 242 | 51 | 289 | 2875 | 51.2 | 0.45 | 225 | 86 |  |
| 6 | 240 | 51 | 287 | 2791 | 51.7 | 0.51 | 204 | 86 |  |
| 7 | 212 | 46 | 201 | 2748 | 50.1 | 0.00 | 521 | 176 | >24 |
| 8 | 239 | 95 | 314 | 2505 | 51.2 | 0.47 | 237 | 165 | >75 |
| Comp. 1 | 265 | 55 | 190 | 2220 | 44.5 | 15.00 | 579 | 229 | 3–5 |

We claim:

1. Integrally asymmetrical hydrophobic membrane for gas exchange composed primarily of at least one polyolefin polymer and having first and second surfaces, the membrane having a support layer with a sponge-like, open-pored, microporous structure and adjacent to this support layer and comprising at least one of the first and second surfaces of the membrane, a separation layer with a structure that is denser than that of the support layer, wherein pores, if any, in the separation layer have an average diameter of <100 nm, wherein the support layer is free of macrovoids and the pores in the support layer are on average essentially isotropic, and wherein the membrane has a porosity in the range of greater than 50% to less than 75% by volume.

2. Process for producing the hydrophobic membrane according to claim 1, the process comprising at least the steps of:
   a) dissolving 20–90% by weight of at least one polyolefin polymer in 80–10% by weight of a solvent system comprised of a mixture of two compounds A and B to form a polyolefin-containing solution by heating to a dissolving temperature that is above a critical demixing temperature $T_c$ of the polyolefin-containing solution, wherein compounds A and B are liquid and miscible at the dissolving temperature, wherein the polyolefin-containing solution of polyolefin polymer and compounds A and B has a miscibility gap in the liquid state of aggregation, wherein compound A is a solvent for the at least one polyolefin polymer, and wherein compound B raises a phase separation temperature of a solution consisting of the at least one polyolefin polymer and compound A,
   b) rendering the polyolefin-containing solution to form a shaped object having first and second surfaces in a die having a temperature above the critical demixing temperature,
   c) cooling the shaped object at such a rate that a thermodynamic non-equilibrium liquid-liquid phase separation is initiated and solidification subsequently occurs, and
   d) removing compounds A and B from the shaped object in order to obtain the hydrophobic membrane from the shaped object,
   wherein compounds A and B are selected such that the boiling point of compound A is at least 50° C. higher than that of compound B, wherein the solvent system has a viscosity at room temperature of less than 60 mPa s, and wherein at least one of the first and second surfaces of the shaped object, after it exits the die and before cooling, is subjected to an atmosphere that promotes the evaporation of compound B.

3. Process according to claim 2, wherein 30–60% by weight of the polymer is dissolved in 70–40% by weight of the solvent system.

4. Process according to claim 2, wherein compound A and compound B have a viscosity of less than 50 mPa s at room temperature.

5. Process according to claim 2, wherein the die temperature is adjusted such that the difference between the boiling point of compound B and the die temperature is between −10° C. and +70° C.

6. Process according to claim 5, wherein the difference is between 0° C. and 40° C.

7. Process according to claim 2, wherein the boiling point of compound A is at least 100° C. higher than that of compound B.

8. Process according to claim 2, wherein cooling occurs in a cooling medium.

9. Process according to claim 8, wherein the cooling medium has a temperature that is at least 100° C. below the critical demixing temperature.

10. Process according to claim 2, wherein the at least one polymer is a polyolefin consisting exclusively of carbon and hydrogen.

11. Process according to claim 10, wherein the at least one polymer is a poly(4-methyl-1-pentene), a polypropylene or a mixture thereof.

12. Process according to claim 11, wherein compound A is dioctyl adipate and compound B is glycerin triacetate.

13. Process according to claim 1 wherein the hydrophobic membrane is a hollow-fiber membrane.

14. Membrane according to claim 1, wherein the membrane structure changes abruptly in the transition from the separation to the support layer.

15. Membrane according to claim 1, wherein the separation layer has a structure in which no pores are detectable under a scanning electron microscope examination at 60000× magnification.

16. Membrane according to claim 1, wherein the support layer is open-pored and the pores have an average diameter between 10 nm and 100 nm.

17. Membrane according to claim 1, wherein the separation layer has a thickness between 0.1 μm and 1 μm.

18. Membrane according to claim 17, wherein the separation layer has a thickness between 0.2 μm and 0.6 μm.

19. Membrane according to claim 1, wherein the porosity of the membrane is in the range from greater than 50% to less than 65% by volume.

20. Membrane according to claim 1, wherein the membrane has an $O_2$ transfer rate of >140 ml/(min*m$^2$) and a $CO_2$ transfer rate of >1900 ml/(min*m$^2$).

21. Membrane according to claim 20, wherein the membrane has an $O_2$ transfer rate of >190 ml/(min*m$^2$) and a $CO_2$ transfer rate of >2200 ml/(min*m$^2$).

22. Membrane according to claim 1, wherein the membrane has a plasma breakthrough time of at least 20 hours.

23. Membrane according to claim 22, wherein the plasma breakthrough time is at least 48 hours.

24. Membrane according to claim 1, wherein the at least one polyolefin polymer is a polyolefin consisting exclusively of carbon and hydrogen.

25. Membrane according to claim 24, wherein the polyolefin is a poly(4-methyl-1-pentene).

26. Membrane according to claim 24, wherein the polyolefin is a polypropylene.

27. Membrane according to claim 24, wherein the membrane consists essentially of a mixture of poly(4-methyl-1-pentene) and a polypropylene.

28. Membrane according to claim 1, wherein the membrane is a hollow-fiber membrane.

29. Membrane according to claim 1, wherein the separation layer comprises only one of the first or second surface of the membrane.

30. membrane according to claim 1, wherein the separation layer comprises both of the first and second surface of the membrane.

31. Process for oxygenating blood, comprising contacting the blood with the membrane according to claim 1 while simultaneously contacting the membrane with oxygen.

* * * * *

UNITED STATES PATENT AND TRADEMARK OFFICE
CERTIFICATE OF CORRECTION

PATENT NO. : 6,409,921 B1
DATED : June 25, 2002
INVENTOR(S) : Marcus Oskar Muller et al.

Page 1 of 1

It is certified that error appears in the above-identified patent and that said Letters Patent is hereby corrected as shown below:

Column 3,
Line 65, insert a space after "6750x" and between "magnification."

Column 16,
Line 51, after "mbar." insert -- Under normal pressure, soybean oil decomposes prior to boiling. An extrapolation of the value for 0.067 mbar to normal pressure would yield a boiling point of over 500°C.) --

Signed and Sealed this

Twenty-ninth Day of October, 2002

*Attest:*

*Attesting Officer*

JAMES E. ROGAN
*Director of the United States Patent and Trademark Office*